United States Patent [19]

Fujii

[11] 4,278,633

[45] Jul. 14, 1981

[54] METHOD OF TREATING A WATER SOLUBLE CAPSULE

[75] Inventor: Akira Fujii, Cincinnati, Ohio

[73] Assignee: Stanley Drug Products, Inc., Portland, Oreg.

[21] Appl. No.: 101,444

[22] Filed: Dec. 10, 1979

Related U.S. Application Data

[63] Continuation of Ser. No. 972,027, Dec. 20, 1978, abandoned, which is a continuation of Ser. No. 857,463, Dec. 5, 1977, abandoned, which is a continuation of Ser. No. 627,027, Oct. 30, 1975, abandoned.

[51] Int. Cl.[3] .......... A61M 3/00

[52] U.S. Cl. .......... 264/134; 53/407; 53/477; 128/261; 128/272; 206/528; 264/232; 264/238; 264/344; 424/37; 427/3; 427/338

[58] Field of Search .......... 264/134, 344, 4, 232, 264/238, 330, 307, 340; 427/3, 338; 128/261, 272; 424/32, 37; 53/477, 407; 206/528

[56] References Cited

U.S. PATENT DOCUMENTS

| | | | |
|---|---|---|---|
| 1,527,659 | 2/1925 | Wilkie | 264/4 |
| 2,064,143 | 12/1936 | Belton et al. | 264/307 |
| 2,318,185 | 5/1943 | Schreyer | 264/307 |
| 2,512,115 | 6/1950 | Senff | 128/261 |
| 2,712,672 | 7/1955 | Calcagno | 264/344 |
| 3,006,760 | 10/1961 | Dersch et al. | 96/107 |
| 3,379,554 | 4/1968 | Brindamour | 427/3 |
| 3,616,101 | 10/1971 | Satchell et al. | 264/4 |

FOREIGN PATENT DOCUMENTS

| | | | |
|---|---|---|---|
| 686229 | 5/1964 | Canada | 264/4 |

OTHER PUBLICATIONS

"Encyclopedia of Chemical Technology"-Kirk-Othmer-Silica Gell, vol. 12, 1968, pp. 345-347.

"Encyclopedia of Chemical Technology"-Kirk-Othmer-Phosphorus Pentoxide, vol. 15, 2-1969, pp. 311-315.

*Primary Examiner*—Jeffery R. Thurlow

*Attorney, Agent, or Firm*—Kinney & Schenk

[57] ABSTRACT

A gelatin capsule is formed with an elongated portion and a bulb portion with a medicinal material therein for supply to a body through inserting the elongated portion in a body orifice. The elongated portion is treated with a hardening agent which withdraws water and/or glycerin from the elongated portion of the capsule so that the elongated portion has sufficient rigidity for insertion within the body orifice. The hardening agent can be a polymer of a glycol, which is preferably polyethylene glycol, an inorganic drying agent such as silica gel or phosphorus pentoxide, an alcohol, or a ketone, such as acetone, for example. When a polymer of a glycol is utilized as the hardening agent, the polymer of a glycol can remain on the elongated portion to function as a lubricant when the elongated portion is inserted in the body orifice. Furthermore, the polymer of a glycol can include an anesthetic for deadening the nerves around the body orifice. To prevent the polymer of a glycol from flowing to the bulb portion to harden it when the polymer of a glycol remains on the elongated portion, the viscosity of the polymer of a glycol is preferably selected so that it will not flow at room temperature although the coating of the polymer of a glycol could be coated with paraffin or a mechanical barrier to prevent this or the bulb portion could be coated with paraffin to prevent the polymer of a glycol from affecting the soft bulb portion or a mechanical barrier could be provided between the elongated and bulb portions.

10 Claims, 6 Drawing Figures

METHOD OF TREATING A WATER SOLUBLE CAPSULE

This is a continuation of prior application Ser. No. 972,027 filed Dec. 12, 1978 (now abandoned) which was a continuation of prior application Ser. No. 857,463, filed Dec. 5, 1977 (now abandoned) which was a continuation of prior application Ser. No. 627,027, filed Oct. 30, 1975 (now abandoned).

In the copending patent application of George S. Sperti et al for "Method For Treating Gelatin Capsules And Product Resulting Therefrom," Ser. No. 511,947, filed Oct. 4, 1974, refiled as now allowed continuation patent application Ser. No. 876,711 and assigned to the same assignee as the assignee of this application, there is shown and described a method of hardening the elongated portion of a gelatin capsule for supplying medicine to a selected area of the body through a body orifice. The invention in the aforesaid Sperti et al application uses a hard gelatin, for example, as the hardening agent.

The present invention is an improvement of the aforesaid Sperti et al application in that a coating material is selected for hardening the elongated portion so that the coating also can function as a lubricant. Furthermore, the lubricant can contain an anesthetic, if needed, such as when dispensing a material for treating hemorrhoids, for example.

Whenever the polymer of a glycol is left on the elongated portion of the capsule until the capsule is used rather than being removed after hardening of the elongated portion, it is necessary to prevent the polymer of a glycol from flowing to the bulb portion so that the bulb portion does not become hard. This can be accomplished through selecting the viscosity of the polymer of a glycol so that it does not flow at room temperature, for example. This also could be prevented by forming a mechanical barrier between the bulb portion and the elongated portion of the capsule. The bulb portion also could be coated with a moisture barrier material such as paraffin, for example, to prevent the polymer of a glycol from flowing to the bulb portion when the polymer of a glycol remains as a coating on the elongated portion.

Instead of hardening the entire elongated portion of the capsule, it should be understood that only a sufficient portion of the periphery of the elongated portion along its entire length needs to be hardened as long as it provides the desired rigidity to the elongated portion. Thus, for example, the polymer of a glycol could be applied to only one half of the periphery of the entire length of the elongated portion. Similarly, the bulb portion need only remain sufficiently soft or flexible to enable deformation thereof by an external pressure so that only a portion thereof need remain soft. Thus, one embodiment of the present invention contemplates applying a polymer of a glycol to one half of the periphery of the entire length of the capsule of half harden the capsule.

While a polymer of a glycol is preferred because of its capability of being utilized as a lubricant, it should be understood that any hardening agent capable of withdrawing water and/or glycerin from the elongated portion of the capsule so as to cause the elongated portion to have sufficient rigidity for insertion within the body orifice can be employed. Thus, the hardening agent can be an inorganic drying agent such as silica gel or phosphorus pentoxide, an alcohol, a ketone, or an acetone, for example.

An object of this invention is to harden a portion of a water soluble capsule so that the hardened portion may be inserted in a body orifice while leaving another portion thereof soft to enable deformation of the soft portion by an external pressure.

Another object of this invention is to harden a portion of a water soluble capsule with a material that not only hardens the portion of the capsule but also functions as a lubricant when the hardened portion is inserted in a body orifice.

A further object of this invention is to harden a portion of a water soluble capsule with a material that not only hardens the portion of the capsule but also functions as a lubricant and may contain an anesthetic when the hardened portion is inserted in a body orifice.

Still another object of this invention is to provide a water soluble capsule having a lubricant on a portion inserted in a body orifice.

A still further object of this invention is to provide a water soluble capsule having a lubricant with an anesthetic on a portion inserted in a body orifice.

Other objects, uses, and advantages of this invention are apparent upon reading this specification, which proceeds with reference to the drawing forming part thereof and wherein.

Figure 1:
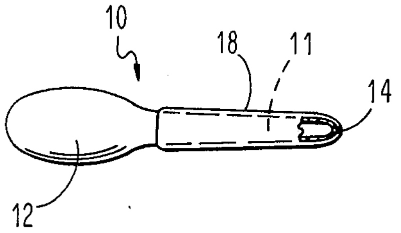
FIG. 1 is a side elevational view, partly in section, of a water soluble capsule having a coating of a polymer of a glycol remaining thereon after hardening.

Referring to the drawing and particularly FIG. 1, there is shown a capsule 10, which is formed of a suitable water soluble material such as gelatin, for example. The capsule 10 is of uniform thickness and hardness throughout prior to being treated by the method of the present invention.

The capsule 10 includes an elongated portion 11 and a bulb portion 12 integral therewith. The end of the elongated portion 11 remote from the bulb portion 12 has opening means such as an aperture 14, for example, to enable the material, which is disposed within the capsule 10, to be dispensed therefrom when an external pressure is applied to the bulb portion 12 of the capsule 10. The quantity of material within the capsule 10 is selected to be the desired dose of medicine, for example, necessary to be applied to an area of the body by supply through a body orifice.

The capsule 10 does not have sufficient rigidity for insertion through a body orifice. Thus, the elongated portion 11 must be hardened so that it will be sufficiently rigid for insertion through a body orifice.

Accordingly, a suitably hardening agent such as a polymer of a glycol, which is preferably polyethylene glycol, is applied to the elongated portion 11 of the capsule 10 to harden the elongated portion 11. The polymer of a glycol can be applied in any suitable manner such as dipping or spraying, for example.

Figure 2:
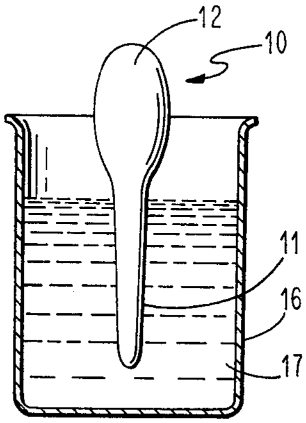
FIG. 2 is a side elevational view, partly in section, showing the application of a polymer of a glycol to the elongated portion of the capsule to harden the elongated portion.

One means of applying a polymer of a glycol is shown in FIG. 2 wherein a tank 16 has a polymer of a glycol 17 therein. By disposing the elongated portion 11 of the capsule 10 within the tank 16, the polymer of glycol 17 is applied only to elongated portion 11. Depending on the viscosity of the polymer of glycol 17, it may be applied by hand rather than being in the tank when its viscosity is such that it will not flow at room temperature, for example. When the polymer of glycol 17 is formed as a liquid in the tank 16, its melting point must be below that of the capsule 10.

The polymer of glycol 17 absorbs water and/or glycerin from the capsule 10 to a sufficient extent to harden the elongated portion 11, which is immersed in the polymer of glycol 17. After the polymer of glycol 17 has remained on the elongated portion 11 for a sufficient period of time to produce the desired hardness of the elongated portion 11, the polymer of glycol 17 can be removed if desired.

If the polymer of glycol 17 is to remain on the elongated portion 11, then its viscosity must be selected so that it will not flow to the bulb portion 12 at room temperature or suitable means must be provided to prevent it from flowing to the bulb portion 12 if the viscosity of the polymer of glycol 17 is such that it would flow to the bulb portion 12 at room temperature. Thus, if the viscosity of the polymer of glycol 17 is utilized to prevent flow when the polymer of glycol 17 forms a coating 18 (see FIG. 1) on the elongated portion 11, the viscosity must be such that the polymer of glycol 17 will not flow at room temperature.

One suitable example of the polymer of glycol 17 is a combination of polyethylene glycol-400 (PEG-400) and polyethylene glycol-4000 (PEG-4000). The parts by weight of each of the two materials in which the elongated portion 11 of each of the capsules 10 was immersed, the period of time that the polymer of glycol 17 remained on the elongated portion 11 of the capsule 10 at room temperature, and the observed degree of hardness obtained by feeling the capsule 10 with 7 being the maximum hardness, 1 being the maximum softness, and 4 indicating the hardness of the capsule 10 when not treated are as follows:

| PARTS BY WEIGHT | | | |
|---|---|---|---|
| PEG-400 | PEG-4000 | TREATMENT TIME IN HOURS | DEGREE OF HARDNESS |
| 495 | 55 | ½ | 4 |
| 495 | 55 | 1 | 5 |
| 495 | 55 | 2 | 6 |
| 495 | 55 | 5 | 7 |
| 495 | 55 | 24 | 7 |
| 460 | 100 | ½ | 4 |
| 460 | 100 | 1 | 5 |
| 460 | 100 | 2 | 6 |
| 460 | 100 | 5 | 7 |
| 460 | 100 | 24 | 7 |
| 400 | 160 | ½ | 4 |
| 400 | 160 | 2 | 6 |
| 300 | 260 | ½ | 4 |
| 300 | 260 | 2 | 6 |
| 200 | 360 | ½ | 4 |
| 200 | 360 | 2 | 6 |

As shown by the foregoing results, the mixtures of PEG-400 and PEG-4000 produce a satisfactory hardness after two hours and a maximum hardness after five hours. The viscosity of PEG-400 is such that it would flow at room temperature so that it must be mixed with PEG-4000 to obtain a viscosity which will not flow at room temperature if the polymer of glycol 17 is to remain on the capsule 10 as the coating 18. The melting point of PEG-4000 is so high that if it were melted it would melt the capsule 10 if not mixed with PEG-400, for example.

To obtain a desired hardness of the elongated portion 11 of the capsule 10, it should be understood that is is not necessary for the polymer of glycol 17 to remain on the capsule 10 as the coating 18. Thus, it is not necessary to use a mixture of PEG-400 and PEG-4000 if the polymer of glycol 17 is not to remain on the capsule 10 as the coating 18 so that only PEG-400 could be employed. When the polymer of glycol 17 is not to remain on the capsule 10, the polymer of glycol 17 is removed by wiping after elapse of a sufficient period of time, which is at least twelve hours, to obtain full hardness of the elongated portion 11 of the capsule 10.

If the polymer of glycol 17 is removed from the elongated portion 11 of the capsule 10 after the elongated portion 11 has completely hardened, the moisture in the bulb portion 12 of the capsule 10 will migrate to the elongated portion 11 even when disposed within a sealed package. Thus, when the polymer of glycol 17 is wiped off after the elongated portion 11 of the capsule 10 has hardened, the shelf life of the capsule 10 unprotected from the atmosphere is relatively short such as one day, for example.

Figure 3:
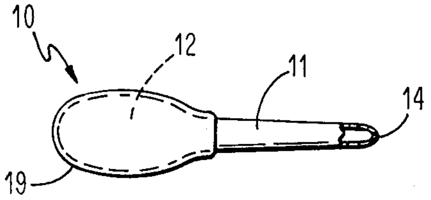
FIG. 3 is a side elevational view, partly in section, of a water soluble capsule after hardening with a coating on its soft portion.

However, if the bulb portion 12 of the capsule 10 has a coating 19 (see FIG. 3) of a moisture barrier material such as paraffin, for example, this will prevent moisture from migrating from the bulb portion 12 to the elongated portion 11. This arrangement also can be utilized when the polymer of glycol 17 remains on the capsule 10 as the coating 18 and has a viscosity such that it would flow at room temperature. Thus, the paraffin would prevent the polymer of glycol 17 from flowing to the bulb portion 12 to harden the bulb portion 12. Instead of applying the paraffin to the bulb portion 12, it could be applied over the coating 18, if desired.

When the polymer of glycol 17 remains on the elongated portion 11 of the capsule 10 as the coating 18 and has a viscosity such that it does not flow at room temperature, it is not necessary to use the moisture barrier material. Instead of using the moisture barrier material on the bulb portion 12 when the polymer of glycol 17 remains on the elongated portion 11 of the capsule 10 as the coating 18 and has a viscosity such that it flows at room temperature, a mechanical barrier could be formed between the bulb portion 12 and the elongated portion 11 to keep the polymer of glycol 17 from flowing to the bulb portion 12 to harden the bulb portion 12.

Figure 4:
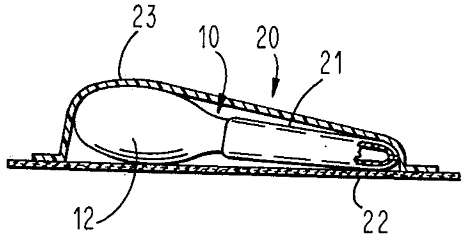
FIG. 4 is a sectional view, partly in elevation, showing the capsule of FIG. 1 disposed within a package.

Referring to FIG. 4, the capsule 10 is shown disposed within a sealed package 20. The capsule 10 has a coating 21 on the elongated portion 11. The coating 21 is formed of a mixture of an anesthetic such as benzocaine, for example, and the polymer of glycol 17. When the anesthetic is benzocaine, it preferably comprises twenty percent by weight of the coating 21. Any material used to form the coating 18 may be readily mixed with benzocaine to form the coating 21.

The coating 21 is particularly useful when employed to supply a medicine for treatment of hemorrhoids. This is because the benzocaine deadens the nerves around the anus into which the hardened elongated portion 11 of the capsule 10 is inserted.

The package 20 preferably comprises a base 22 of a suitable material such as cardboard, for example, and a top 23 of a suitable moisture proof material, preferably transparent, such as plastic or wax paper, for example. The base 22 and the top 23 are sealed to each other by a suitable material such as paraffin wax, for example.

Thus, the coating 21 not only functions as an anesthetic but also as a lubricant during insertion of the hardened elongated portion 11 of the capsule 10 into the anus, for example. The viscosity of the coating 21 is similar to that of the viscosity of petroleum jelly.

While it is preferred that the elongated portion 11 be hardened around its entire periphery, it should be understood that such is not a requisite for satisfactory operation. It is only necessary for the elongated portion 11 of the capsule 10 to have sufficient rigidity for insertion in a body orifice and the bulb portion 12 to have sufficient flexibility to enable deformation thereof by application of an external pressure.

Figure 5:
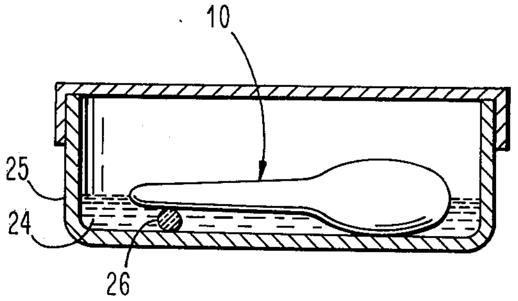
FIG. 5 is a sectional view showing another method of hardening a portion of the entire length of the capsule.

Accordingly, as shown in FIG. 5, about half of the entire length of the capsule 10 may be immersed along its entire length within a mixture 24 of PEG-400 and PEG-4000. The capsule 10 is disposed within the mixture 24, which is in a tank 25. The elongated portion 11 is supported by suitable means such as a pillow 26 to dispose about one half of the periphery of the entire length of the capsule 10 within the mixture 24. This arrangement results in the capsule 10 being half hardened along its entire length. As a result, the elongated portion 11 has sufficient rigidity to enter a body orifice while the bulb portion 12 retains sufficient flexibility around one half thereof to allow sufficient deformation of the bulb portion 12 by application of an external pressure to dispense the material within the capsule 10 therefrom.

The pillow 26 is formed of a suitable material which is not affected by a polymer of a glycol. Thus, the pillow 26 could be formed of glass or polyethylene, for example.

Tests have been conducted on capsules in which PEG-400 and PEG-4000 are mixed and the capsule 10 immersed as shown in FIG. 5. The results of these tests with the parts by weight of each of the two materials forming the mixture 24, the period of time that the capsule 10 remained in the mixture 24, and the observed degree of hardness obtained by feeling the capsule 10 with 7 being the maximum hardness, 1 being the maximum softness, and 4 indicating the hardness of the capsule 10 when not treated are as follows:

| PARTS BY WEIGHT | | | |
|---|---|---|---|
| PEG-400 | PEG-4000 | TREATMENT TIME IN HOURS | DEGREE OF HARDNESS |
| 495 | 55 | 2 | 5 |
| 495 | 55 | 5 | 6 |
| 495 | 55 | 24 | 7 |
| 495 | 55 | 48 | 7 |
| 460 | 100 | 2 | 5 |
| 460 | 100 | 5 | 6 |
| 460 | 100 | 24 | 7 |
| 460 | 100 | 48 | 7 |
| 400 | 160 | 2 | 5 |
| 400 | 160 | 24 | 7 |
| 300 | 260 | 2 | 5 |
| 300 | 260 | 24 | 7 |
| 200 | 360 | 2 | 5 |
| 200 | 360 | 24 | 7 |

While the present invention has shown and described the polymer of glycol 17 as preferably being polyethylene glycol, it should be understood that the invention is not limited to polyethylene glycol. Thus, the polymer of glycol 17 could be polypropylene glycol, for example.

While the hardening of the elongated portion 11 of the capsule 10 has been described as being by use of the polymer of glycol 17, it should be understood that any hardening agent which withdraws water and/or glycerin from the elongated portion 11 of the capsule 10 can be employed. For example, an inorganic drying agent such as silica gel or phosphorus pentoxide, and alcohol, or a ketone such as acetone may be utilized as the hardening agent instead of the polymer of glycol 17.

Tests have been made to determine the hardness of gelatin capsules with which various hardening agents were utilized and compared with the use of water and a mixture of PEG-400 and PEG-4000. The results of these tests with the observed degree of hardness obtained by feeling the capsule with +6 being the maximum hardness, −6 being the maximum softness, 0 indicating the hardness of the capsule when not treated, and * indicating that the capsule is softened and enlarged are as follows:

| | Observations after Preparation | | | | |
|---|---|---|---|---|---|
| | 2.5 hr | 5 hr | 1 day | 5 days | 10 days |
| water | −4 | −6 | −6 | * | * |
| 10% ethanol | −4 | −6 | −6 | * | * |
| 20% ethanol | −3 | −4 | −6 | * | * |
| 30% ethanol | −3 | −4 | −6 | * | * |
| 40% ethanol | −3 | −4 | −5 | * | * |
| 50% ethanol | −2 | −3 | −4 | * | * |
| 60% ethanol | −2 | −3 | −4 | −6 | * |
| 70% ethanol | −1 | −2 | −2 | −2 | −4 |
| 80% ethanol | −1 | −1 | 0 | 0 | 0 |
| 90% ethanol | 0 | 0 | +1 | +1 | +2 |
| 100% ethanol | +2 | +4 | +6 | +6 | +6 |
| methanol | +1 | +1 | +4 | −4 | +6 |
| n-propanol | +2 | +3 | +4 | +5 | +6 |
| i-propanol | +2 | +3 | +4 | +5 | +6 |
| m-butanol | +2 | +3 | +4 | +4 | +6 |
| n-estanol | +1 | +2 | +3 | −3 | +4 |
| decylalcohol | +1 | +2 | +3 | +4 | +4 |
| acetone | +2 | +3 | +4 | +5 | +6 |
| methylethyl ketone | +2 | +3 | +4 | +5 | +6 |
| silica gel | +2 | +3 | +4 | +6 | +6 |
| phosphorus pentoxide | +2 | +4 | +6 | +6 | +6 |
| 4 parts of PEG-400 to 1 part of PEG-4000 by weight | +1 | +3 | +6 | +6 | +6 |

Figure 6:
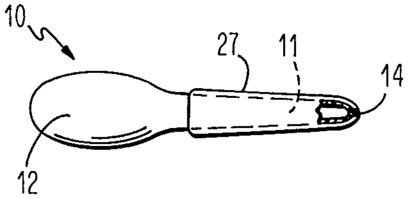
FIG. 6 is a side elevational view, partly in section, of a water soluble capsule after hardening with a coating on the hardened portion.

When coating the elongated portion 11 of the capsule 10 with an anhydrous alcohol, it has been found that the elongated portion 11 remained hard for about ten days. If a shelf life longer than ten days is required for an anhydrous alcohol, for example, then a coating 27 of a moisture barrier material is applied over the elongated portion 11 as shown in FIG. 6. The coating 27 can be polyethylene glycol or paraffin, for example.

If the capsule 10 of FIG. 6 is disposed within the sealed package 20 as shown in FIG. 4, then it is not necessary to utilize any moisture in the atmosphere from being added to cause softening of the hardened elongated portion 11.

While the hardening agent has been indicated as being an alcohol or ketone, for example, it should be understood that a mixture of alcohols or a mixture of ketones could be employed. Similarly, a mixture of an alcohol and a ketone, a mixture of a plurality of alcohols and a single ketone, or a mixture of a plurality of ketones and a single alcohol also could be utilized as the hardening agent.

It should be understood that the capsule 10 could be formed of any water soluble material. It is not necessary that it be formed of gelatin.

An advantage of this invention is that it enables easier insertion of a medicinal dispenser into a body orifice. Another advantage of this invention is that is remains hard for a relatively long period of time. Still another advantage of this invention is that it has both a lubricant and an anesthetic provided in a coating utilized to provide the desired rigidity of the elongated portion inserted into the body orifice.

For purposes of exemplification, particular embodiments of the invention have been shown and described according to the best present understanding thereof. However, it will be apparent that changes and modifications in the arrangement and construction of the parts thereof may be resorted to without departing from the spirit and scope of the invention.

What is claimed is:

1. A method of treating a water soluble gelatin capsule of the type used for supplying a material to a selected area of the body through a body orifice, said capsule having a soft deformable bulb portion and an elongated portion insertable through said orifice, said method comprising the steps of applying a hardening agent as a coating to a sufficient portion of the periphery of said elongated portion to provide a desired rigidity to said elongated portion for insertion through said orifice, said hardening agent being a mixture of polyethylene glycol-400 and polyethylene glycol-4000, which mixture does not flow at room temperature.

2. The method according to claim 1 in which said hardening agent is applied to the entire periphery and substantially the entire length of the elongated portion.

3. The method according to claim 2 including the additional step of coating the bulb portion of the capsule with a moisture barrier material.

4. The method according to claim 2 including the additional step of applying paraffin as a moisture barrier material over the coating of said hardening agent.

5. The method according to claim 2 wherein prior to the application of the coating an anesthetic is mixed with said hardening agent.

6. The method according to claim 2 including the additional steps of removing the coating of said hardening agent from said elongated portion after the desired hardness is produced and coating the bulb portion of the capsule with a moisture barrier material.

7. The method according to claim 6 wherein said moisture barrier material is paraffin.

8. The method according to claim 2 including the additional step of disposing the capsule within a moisture sealed package after said elongated portion has hardened.

9. The method according to claim 2 including retaining the hardening agent on the elongated portion of the capsule after it is applied and preventing the hardening agent from acting on the bulb portion of the capsule.

10. The method according to claim 1 including applying a moisture barrier material over the elongated portion having the hardening agent applied thereto.

* * * * *